US00PP34909P2

(12) United States Plant Patent
van Langen

(10) Patent No.: US PP34,909 P2
(45) Date of Patent: Jan. 10, 2023

(54) ***ECHEVERIA* PLANT NAMED 'AMIECH2106'**

(50) Latin Name: ***Echeveria secunda* var. *pumila* x *lilacina***
Varietal Denomination: AMIECH2106

(71) Applicant: NovoAmi B.V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 17/803,333

(22) Filed: May 14, 2022

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct *Echeveria* hybrid plant named 'AMIECH2106' which is characterized by succulent foliage loosely arranged in a basal rosette, strongly glaucous foliage at and near the center of the rosette with a very light blue-grey to greyed-green general appearance that becomes progressively darker blue-grey to greyed-green as the foliage matures towards the outer whorls of the rosette, near-white foliar margins at and near the center of the rosette that become suffused with greyed-purple as the foliage matures towards the outer whorls of the rosette, and the stability of these characteristics from generation to generation.

4 Drawing Sheets

Latin name of the genus and species: The Latin name of the genus and species of the novel variety disclosed herein is *Echeveria secunda* var. *pumila* x *lilacina*.

Variety denomination: The inventive variety of *Echeveria* hybrid disclosed herein has been given the variety denomination 'AMIECH2106'.

BACKGROUND OF THE INVENTION

Parentage: 'AMIECH2106' is an interspecific hybrid seedling selection resulting from the controlled pollination of *Echeveria secunda* var. *pumila* (not patented), the seed parent, with an unnamed *Echeveria lilacina* plant (not patented), the pollen parent. The crossing was made by the inventor in the spring of 2017 at a commercial greenhouse in Heerhugowaard, the Netherlands. In the spring of 2018, one seedling was observed which exhibited unique growth and foliage characteristics. The seedling was isolated for further evaluation in order to confirm the distinctness and stability of the characteristics first observed. Upon confirmation of distinctness and stability, 'AMIECH2106' was selected for commercialization.

Asexual Reproduction: Asexual reproduction of the new cultivar 'AMIECH2106', by way of rooting leaf cuttings, was first initiated in the spring of 2019 at the inventor's commercial greenhouse in Heerhugowaard, the Netherlands. Through five subsequent generations, the unique features of this cultivar have proven to be stable and true to type.

SUMMARY OF THE INVENTION

The cultivar 'AMIECH2106' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2106'. These characteristics in combination distinguish 'AMIECH2106' as a new and distinct *Echeveria* hybrid cultivar:

1. 'AMIECH2106' exhibits long, oblanceolate foliage loosely held in a basal rosette; and
2. 'AMIECH2106' exhibits a relatively fast rate of growth; and
3. 'AMIECH2106' exhibits strongly glaucous juvenile foliage at and near the center of the rosette, with a very light blue-grey to greyed-green general appearance; and
4. 'AMIECH2106' exhibits foliage that becomes progressively darker blue-grey to greyed-green as the foliage matures towards the outer whorls of the rosette; and
5. 'AMIECH2106' exhibits mature foliage at the outermost whorls of the rosette that is colored with a mixture of yellow-green and greyed-green and lightly covered with blue-grey to greyed-green epicuticular wax; and
6. 'AMIECH2106' exhibits foliar margins at and near the center of the rosette which have a near-white general appearance, which become suffused with greyed-purple as the foliage matures towards the outer whorls of the rosette.

BOTANICAL DESCRIPTION OF THE PLANT

Figure 1:
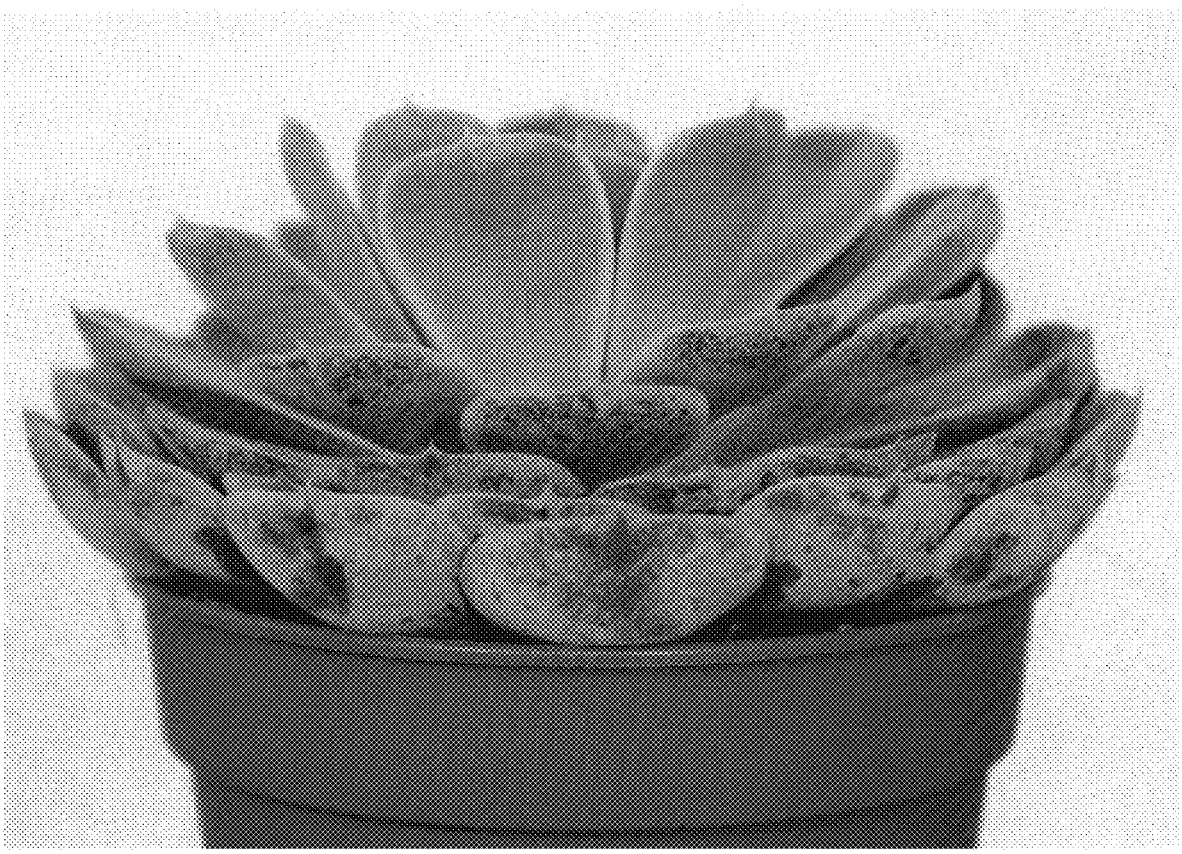
FIG. 1 illustrates, as nearly true as it is reasonably possible to make the same in color photographs of this type, an exemplary plant of 'AMIECH2106' grown in a commercial greenhouse in Heerhugowaard, the Netherlands. This plant is approximately 25 weeks old, shown planted in a 12 cm container.
Figure 2:
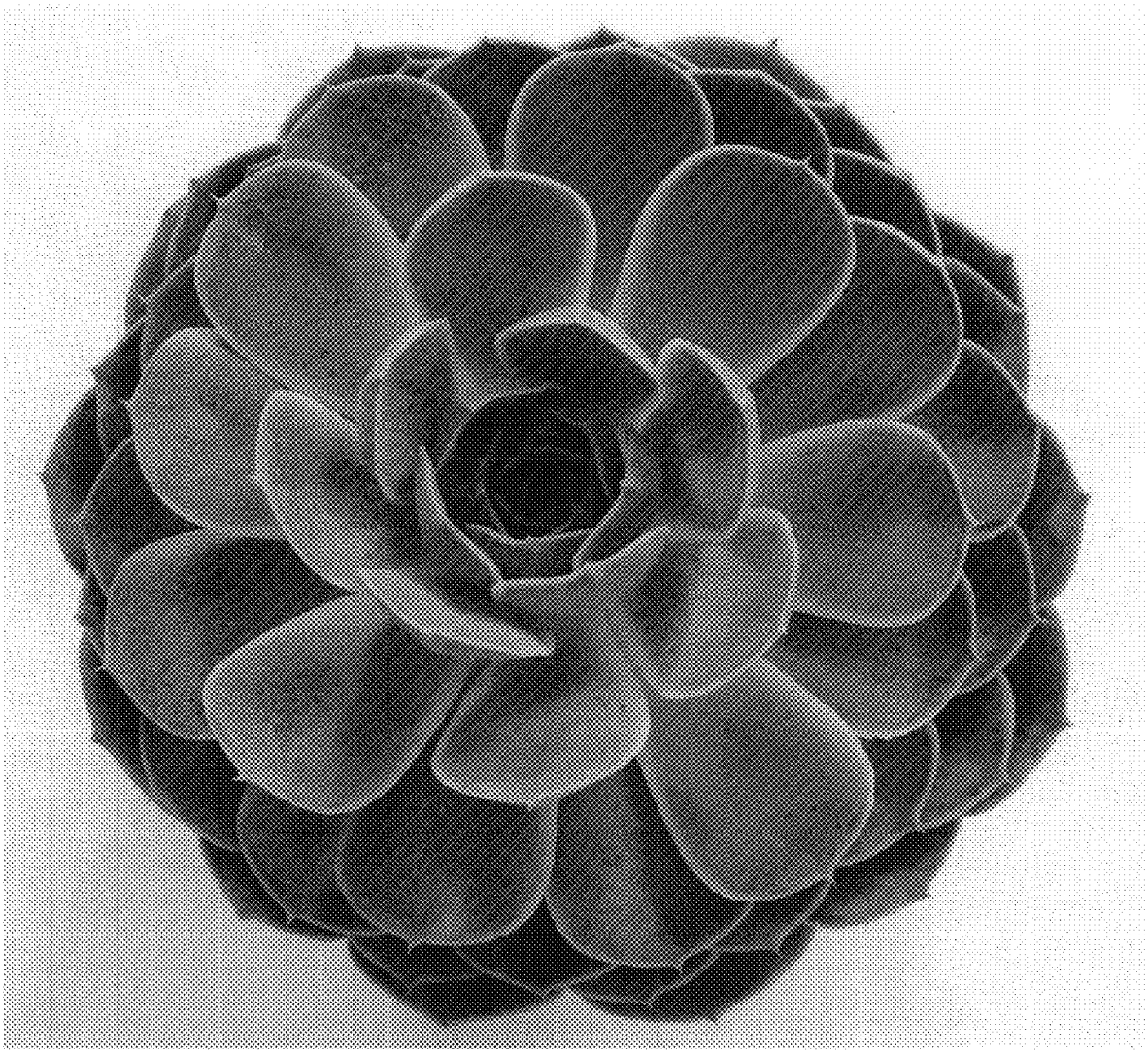
FIG. 2 illustrates, as nearly true as it is reasonably possible to make the same in color photographs of this type, the typical foliage arrangement of 'AMIECH2106.
Figure 3:
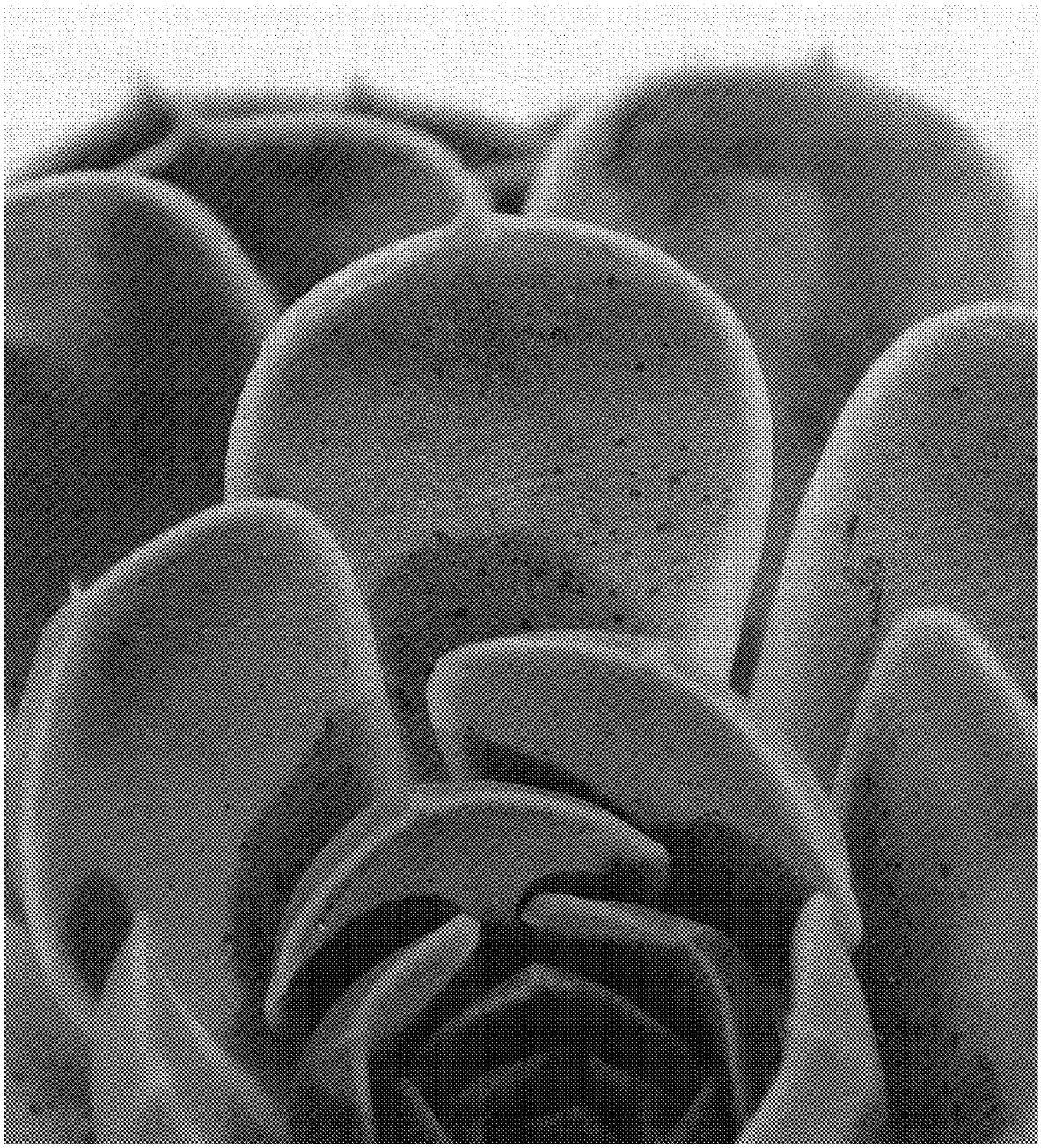
FIG. 3 illustrates, as nearly true as it is reasonably possible to make the same in color photographs of this type, the adaxial surface of the mature foliage 'AMIECH2106'.
Figure 4:
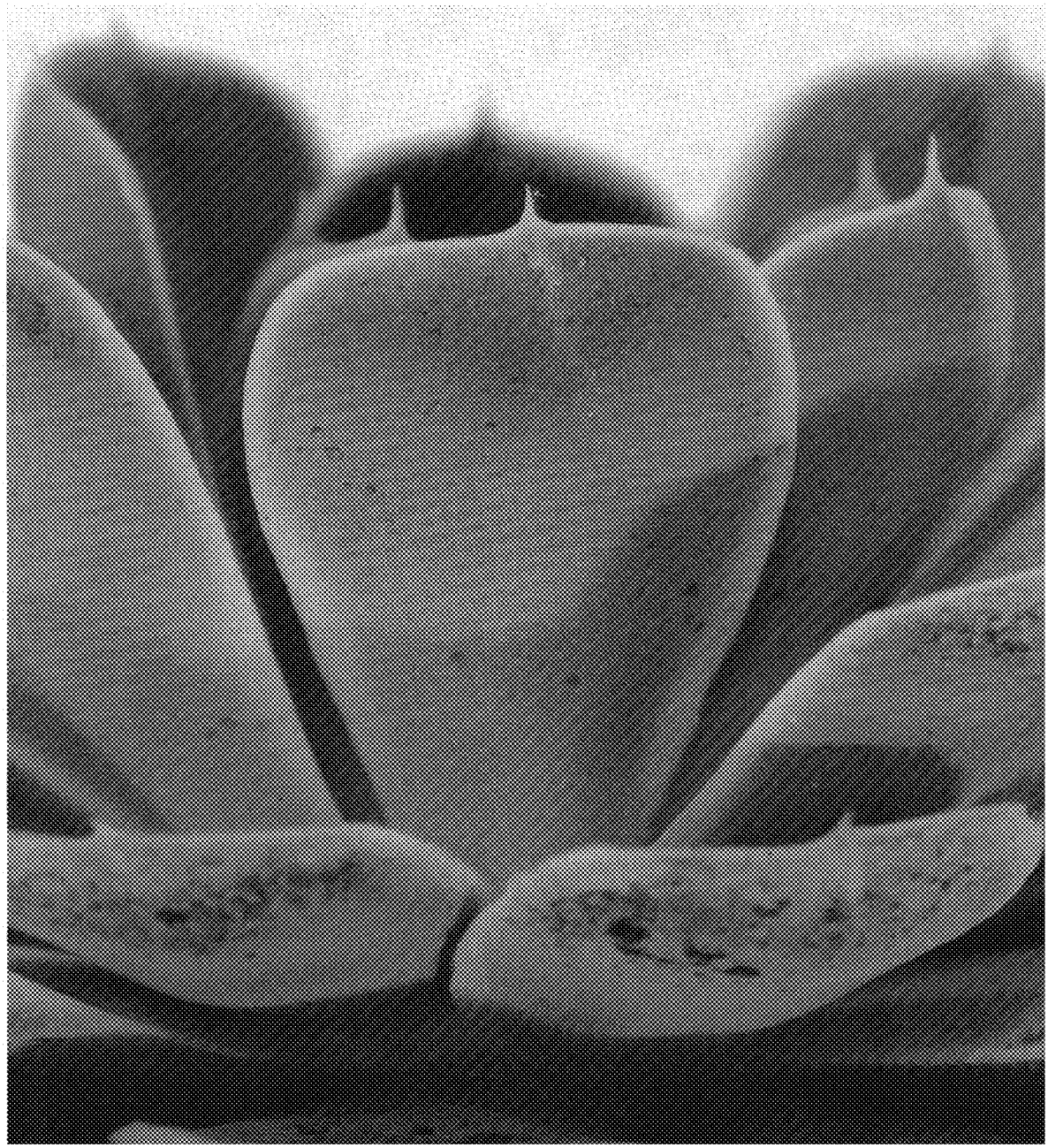
FIG. 4 illustrates, as nearly true as it is reasonably possible to make the same in color photographs of this type, the abaxial surface of the mature foliage 'AMIECH2106'.

The following observations and measurements made in February of 2022 describe averages from a sampleset of six specimens of 25-week-old 'AMIECH2106' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2106' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'AMIECH2106' and comparisons with the parent plants and closest known comparator are provided below.

Plant description:

*Growth habit.*—Succulent perennial with foliage growing in a non-branched basal rosette.

*Plant shape.*—Flattened to flattened globular.

*Height from soil level to top of foliar plane.*—6.6 cm.

*Plant spread.*—Average of 14.8 cm.

*Growth rate.*—Fast growing.

*Plant vigor.*—Moderately vigorous.

*Propagation.*—Type — Leaf cuttings. Time to initiate rooting — Approximately 21 days at 18 degrees Celsius. Crop time — Approximately 20 weeks to produce a marketable plant in a 7 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosette; no main branches or lateral branches present.

Foliage:

*Arrangement.*—Rosette.

*Division.*—Simple.

*Attachment.*—Sessile.

*Quantity.*—Approximately 80 leaves per rosette.

*Shape.*—Oblanceolate.

*Dimensions.*—6.9 cm long, 2.75 cm wide, and 0.7 cm thick, on average.

*Aspect.*—Very slightly concave and curled upward, distally.

*Attitude.*—Juvenile foliage at the center of the rosette is held upward and outward; foliage becomes progressively more relaxed towards the outer whorls of mature foliage which lay nearly horizontal.

*Apex.*—Apiculate.

*Base.*—Long cuneate.

*Margin.*—Entire to very slightly crenulate.

*Pubescence, texture and luster of the adaxial surface.*—Smooth, glabrous, glaucous, and matte.

*Pubescence, texture and luster of the abaxial surface.*—Smooth, glabrous, glaucous, and matte.

*Color.*—Juvenile foliage, adaxial surface — Yellow-green, nearest to RHS 147A; fading to a lighter shade of yellow-green towards the base, nearest to a combination of RHS 146C and 145D; margined light yellow-green, nearest to RHS 147D. Leaves are heavily covered with a relatively thick layer of epicuticular wax which is colored with a mixture of blue-green and greyed-green, RHS 122A and N189A. Juvenile foliage, abaxial surface — Yellow-green, nearest to RHS 147A; fading to a lighter shade of yellow-green towards the base, nearest to RHS 145D; margined light yellow-green, nearest to RHS 147D. Leaves are heavily covered with a relatively thick layer of epicuticular wax which is colored with a mixture of blue-green and greyed-green, RHS 122B and N189C. Mature foliage, adaxial surface — Yellow-green, nearest to RHS 147A; fading to a lighter shade of yellow-green towards the base, nearest to a combination of RHS 147C and 147D; margined greyed-green, nearest to RHS 192A, and becoming lightly suffused with greyed-purple distally, nearest to RHS 186D. Leaves are heavily covered with a relatively thick layer of epicuticular wax which is colored with a mixture of blue-green and greyed-green, RHS 122A and N189A. Mature foliage, abaxial surface — Nearest to a mixture of yellow-green and greyed-green, RHS 147A and N189A; fading to a lighter shade of yellow-green towards the base, nearest to RHS 147D; margined greyed-green, nearest to RHS 192A, and becoming lightly suffused with greyed-purple distally, nearest to RHS 186D. Leaves are heavily covered with a thin layer of epicuticular wax which is colored with a mixture of blue-green and greyed-green, RHS 122B and N189C. Venation, adaxial surface — No visible venation. Venation, abaxial surface — No visible venation.

*Petiole.*—No petiole; leaves are sessile.

Inflorescence: No flowering has been observed to date.

Comparisons with the parent plants and closest known comparator: Plants of the new cultivar 'AMIECH2106' differ from the seed parent, an *Echeveria secunda* var. *pumila* (not patented), in the following characteristics described in Table 1 below.

TABLE 1

| Characteristic | 'AMIECH2106' | The seed parent. |
|---|---|---|
| Foliage width. | Broader than the seed parent. | Narrower than 'AMIECH2106'. |
| General coloration of the adaxial surface of the mature foliage. | The thick layer of blue-green to greyed-green epicuticular wax cover the yellow-green to greyed-green foliage creates a blue-grey to blue-green general appearance. | Nearest to in between g blue-reen and greyed-green, and moderately to heavily suffused with red. |

Plants of the new cultivar 'AMIECH2106' differ from the pollen parent, an unnamed *Echeveria lilacina* plant (not patented), in the following characteristics described in Table 2 below.

TABLE 2

| Characteristic | 'AMIECH2106' | The pollen parent. |
|---|---|---|
| Foliage length. | Longer than the pollen parent. | Shorter than 'AMIECH2106'. |
| Foliage width. | Narrower than the pollen parent. | Broader than 'AMIECH2106'. |
| General coloration of the adaxial | The thick layer of blue-green to greyed-green epicuticular wax cover the yellow-green | Pale greyed-green with a slight cyanic hue, and lightly suf- |

TABLE 2-continued

| Characteristic | 'AMIECH2106' | The pollen parent. |
|---|---|---|
| surface of the mature foliage. | to greyed-green foliage creates a blue-grey to blue-green general appearance. | fused with pale pink. |

Comparisons with the closest known comparator: Plants of the new cultivar 'AMIECH2106' differ from the closest known commercial comparator, *Echeveria* hybrid 'Pullox' (not patented), in the following characteristics described in Table 3 below.

TABLE 3

| Characteristic | 'AMIECH2106' | 'Pullox' |
|---|---|---|
| Foliage abundance. | More abundant than 'Pullox'. | Less abundant than 'AMIECH2106'. |
| Foliage attitude. | More upright than 'Pullox'. | More relaxed than 'AMIECH2106'. |
| Foliage width. | Narrower than 'Pullox'. | Broader than 'AMIECH2106'. |
| General coloration of the adaxial surface of the mature foliage. | The thick layer of blue-green to greyed-green epicuticular wax cover the yellow-green to greyed-green foliage creates a blue-grey to blue-green general appearance. | Light greyed-white and lightly suffused with pink. |

That which is claimed is:

1. A new and distinct variety of *Echeveria secunda* var. *pumila* x *lilacina* plant named 'AMIECH2106', substantially as dscribed and illustrated herein.

* * * * *